(12) United States Patent
Blake

(10) Patent No.: US 12,171,672 B2
(45) Date of Patent: *Dec. 24, 2024

(54) BONE GRAFT MATERIAL LOADING ASSEMBLY AND ASSOCIATED DEVICES, SYSTEMS, AND METHODS

(71) Applicant: Orthofix US LLC, Lewisville, TX (US)

(72) Inventor: Stephen Vincent Blake, Allen, TX (US)

(73) Assignee: Orthofix US LLC, Lewisville, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/336,460

(22) Filed: Jun. 16, 2023

(65) Prior Publication Data
US 2023/0404776 A1 Dec. 21, 2023

Related U.S. Application Data

(63) Continuation of application No. 17/343,389, filed on Jun. 9, 2021, now Pat. No. 11,679,002.

(60) Provisional application No. 63/037,719, filed on Jun. 11, 2020.

(51) Int. Cl.
*A61F 2/46* (2006.01)
(52) U.S. Cl.
CPC .................................. *A61F 2/4601* (2013.01)
(58) Field of Classification Search
CPC ............... A61F 2/4601; A61B 17/8802; A61B 17/8822; A61B 17/8827
See application file for complete search history.

(56) References Cited

U.S. PATENT DOCUMENTS

| | | | |
|---|---|---|---|
| 4,787,891 A | 11/1988 | Levin et al. | |
| 5,282,793 A | 2/1994 | Larson | |
| 6,939,330 B1 | 9/2005 | McConnell-Montalvo et al. | |
| 7,740,632 B2 | 6/2010 | Young | |
| 7,744,270 B2 * | 6/2010 | Plishka | B01F 33/50112 366/195 |
| 7,946,417 B2 * | 5/2011 | Plishka | B01F 35/562 604/87 |

(Continued)

OTHER PUBLICATIONS

Chilean Patent Office, First Substantive Examination Report for Chile Application No. 2022-03469, dated Mar. 5, 2024, 12 pages.

(Continued)

*Primary Examiner* — Anu Ramana
(74) *Attorney, Agent, or Firm* — Haynes and Boone, LLP

(57) ABSTRACT

A bone graft loading device includes a syringe comprising a nozzle at a distal portion of the syringe and an opening at a proximal portion of the syringe, and a plunger configured to force bone graft material from the reservoir through the nozzle. The plunger comprises a plunger body positioned at least partially within the syringe and defining a lumen. A tamp is positioned within the lumen of the plunger body and is configured to protrude distally of the plunger through the nozzle. The plunger mates with an inner wall of the syringe and the tamp to block passage of the bone graft material into the lumen of the plunger body. The plunger can be rotated to guide the bone graft material into the cannula, and the tamp can be periodically actuated to clear clogs that form at or near the nozzle.

11 Claims, 7 Drawing Sheets

(56) References Cited

U.S. PATENT DOCUMENTS

| | | | |
|---|---|---|---|
| 8,021,037 B2* | 9/2011 | Krueger | A61B 17/8822 366/195 |
| 8,821,505 B2* | 9/2014 | Donovan | A61B 17/8816 606/93 |
| 8,967,854 B2* | 3/2015 | Sand | B01F 33/50115 366/192 |
| 9,095,394 B2 | 8/2015 | Click et al. | |
| 9,545,281 B2* | 1/2017 | Donovan | A61B 17/8816 |
| 10,172,660 B2 | 1/2019 | Lou et al. | |
| 10,271,962 B2* | 4/2019 | Heald | A61L 27/54 |
| 10,709,579 B2* | 7/2020 | Heald | A61B 17/8819 |
| 11,116,647 B2* | 9/2021 | Greenhalgh | A61B 17/1659 |
| 2005/0282117 A1 | 12/2005 | Aravena et al. | |
| 2007/0010824 A1 | 1/2007 | Malandain et al. | |
| 2007/0093759 A1 | 4/2007 | Sickler | |
| 2009/0149860 A1* | 6/2009 | Scribner | A61B 17/8822 606/92 |
| 2011/0264099 A1 | 10/2011 | Quinto | |
| 2014/0358188 A1 | 12/2014 | Larson et al. | |
| 2014/0378937 A1 | 12/2014 | Anderson et al. | |
| 2016/0051306 A1 | 2/2016 | Sasaki | |

OTHER PUBLICATIONS

International Searching Authority, International Search Report and Written Opinion of the International Searching Authority, International Application No. PCT/US21/36816, Sep. 30, 2021, 8 pages, ISA/US.

European Patent Office, Extended European Search Report for EP21823099.3, dated Jun. 5, 2024, 8 pages.

\* cited by examiner

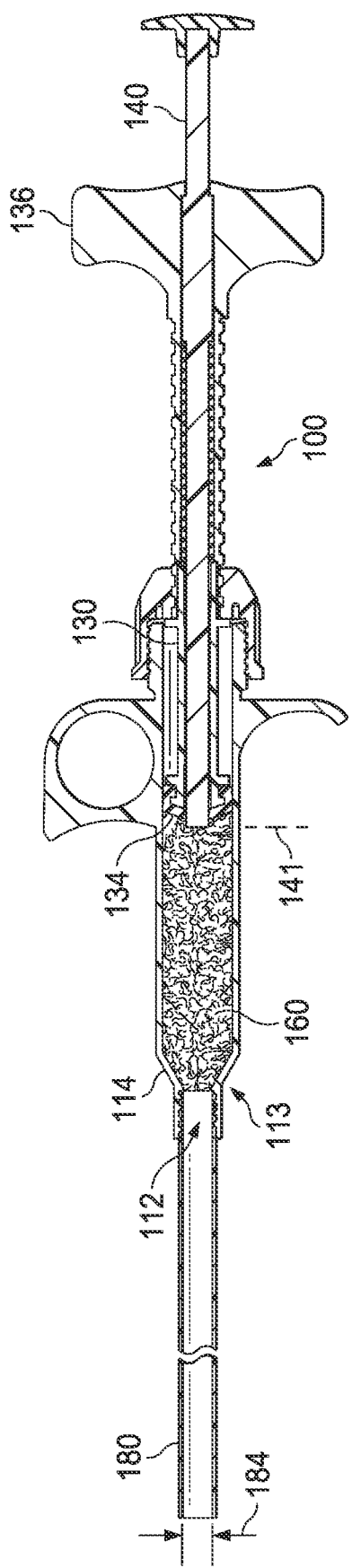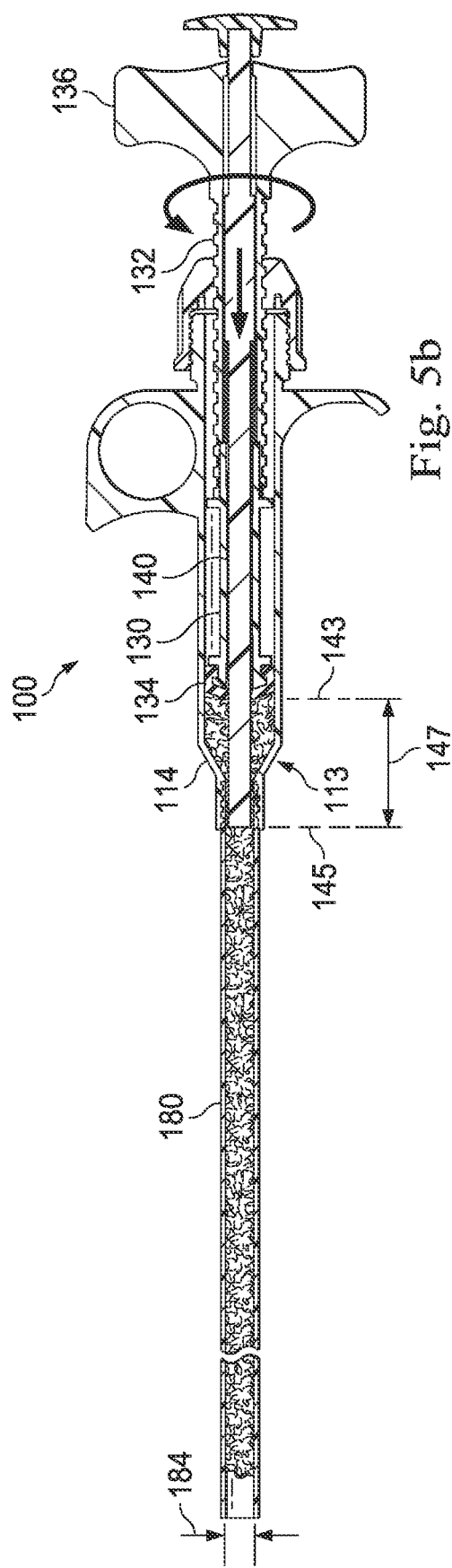

BONE GRAFT MATERIAL LOADING ASSEMBLY AND ASSOCIATED DEVICES, SYSTEMS, AND METHODS

CROSS-REFERENCE TO RELATED APPLICATIONS

This present application is a continuation of U.S. patent application Ser. No. 17/343,389, filed Jun. 9, 2021 which claims priority to and the benefit of U.S. Provisional Patent Application No. 63/037,719, filed Jun. 11, 2020, the entirety of which is hereby incorporated by reference.

TECHNICAL FIELD

The present disclosure relates generally to assemblies and devices for loading and delivering biological material to a patient. More specifically, the present disclosure provides assemblies and devices for loading bone graft material into an injection cannula.

BACKGROUND

One important surgical tool in the treatment of bone-related medical issues is to provide bone graft material to anatomical structures affected during surgical procedures to aid in the bone regeneration process and to promote healing. It is desirable to be precise and accurate in the delivery of the bone graft site. However, bone graft materials may not be easily workable. For example, bone graft materials may be heterogenous mixtures of tissue and fluids that are not easily compressed or moved by injection. In some instances, an injection tube or cannula is used to inject the bone graft material with a higher degree of control and precision. Loading the bone graft material into the injection tube can be an imprecise and difficult process. If too much force is applied to the bone graft material when it is being loaded into the injection tube, the fluids of the bone graft material mixture can be expressed, which adversely affects the qualities and workability of the material. Further, bone graft material may be prone to clogs or stoppages, particularly when the bone graft material is being moved into a tube or reservoir of a smaller cross-sectional size.

SUMMARY

The present application provides devices, assemblies, and associated methods for loading bone graft material into a bone graft injection cannula. In one embodiment, a bone graft loading device comprises a syringe, a threaded plunger configured to force bone graft material toward a nozzle of the syringe, and a tamp configured to protrude out a distal end of the plunger to force the bone graft material through the nozzle and into a cannula coupled to the nozzle of the syringe. The tamp is coupled to the plunger and the syringe such that the tamp can move independently of the plunger. In an exemplary embodiment, a physician can use the threaded plunger as the main mechanism to guide the bone graft material into the cannula, and may periodically switch to the tamp to clear clogs that form at or near the nozzle.

According to one embodiment, a bone graft loading device includes a syringe defining a reservoir, the syringe comprising a nozzle at a distal portion of the syringe and an opening at a proximal portion of the syringe, and a plunger configured to force bone graft material from the reservoir through the nozzle. The plunger comprises a plunger body positioned at least partially within the syringe and defining a lumen; a handle coupled to a proximal end of the plunger body and positioned outside the reservoir; and a tamp positioned within the lumen of the plunger body and configured to protrude distally of the plunger through the nozzle. An outer surface of the plunger mates with an inner wall of the syringe, and an inner surface of the plunger mates with the tamp to block passage of the bone graft material into the lumen of the plunger body.

In some embodiments, the plunger comprises a stopper coupled to a distal end of the plunger body. In some embodiments, the stopper comprises: the outer surface of the plunger mating with the inner wall of the syringe; and the inner surface of the plunger mating with the tamp. In some embodiments, the plunger body comprises a threaded portion and a distal portion coupled to the threaded portion, wherein at least the distal portion extends within the syringe. In some embodiments, in a retracted position, at least part of the threaded portion is positioned outside of the syringe. In some embodiments, the distal portion of the plunger body comprises a flange.

In some embodiments, the bone graft loading device further comprises a spring coupled to the tamp and the plunger, wherein the spring is configured to bias the tamp in a proximal direction relative to the plunger. In some embodiments, the tamp comprises a widened section and a distal section, a cross-sectional size of the widened section is greater than a cross-sectional size of the distal section, the plunger body comprises a first retention feature around the lumen of the plunger body, and the spring is positioned around the distal section of the tamp and extends between the first retention feature of the plunger body and the widened section of the tamp. In some embodiments, the plunger comprises a second retention feature proximal of the first retention feature, and wherein second retention feature is configured to abut a surface of the widened section of the tamp to retain the tamp within the lumen of the plunger body. In some embodiments, the syringe comprises a finger grip feature protruding from an external surface of the syringe. In some embodiments, the tamp is configured to advance distally relative to the plunger by a first distance, and wherein a distal end of the tamp is spaced from the nozzle by a distance greater than the first amount when the plunger is in a first position relative to the syringe. In some embodiments, the first distance is between 1.0 in. and 2.0 in. In some embodiments, a proximal section of the tamp extends proximally of the lumen of the plunger body, and wherein a tamp cap is coupled to the proximal section of the tamp. In some embodiments, the tamp cap is positioned proximally of the handle of the plunger and is movable independently of the handle.

According to another embodiment of the present disclosure, a method for loading a bone graft injection cannula includes: coupling the cannula to a syringe defining a reservoir, the syringe comprising a nozzle at a distal portion of the syringe and an opening at a proximal portion of the syringe; placing bone graft material within the reservoir; providing a plunging assembly that comprises: a plunger body defining a lumen; a handle coupled to a proximal end of the plunger body; a tamp extending within the lumen of the plunger body, wherein the tamp is movable relative to the plunger body, and wherein the tamp is biased proximally relative to the plunger body; coupling the plunging assembly to the syringe such that the plunger body is positioned within the reservoir through the opening at the proximal portion, wherein an outer surface of the plunger is configured to form a first sliding seal with the reservoir wherein an inner surface of the plunger is configured to form a second sliding seal with the tamp; rotating the handle of the plunger assembly to move the bone graft material toward the nozzle; and pushing the tamp toward the nozzle such that a distal end of the tamp protrudes distally of the plunger body to force the bone graft material through the nozzle and into the cannula.

According to another embodiment of the present disclosure, a bone graft loading device includes: a syringe defining a reservoir, the syringe comprising a nozzle at a distal portion of the syringe and an opening at a proximal portion of the syringe, wherein the syringe comprises a first cylindrical portion comprising a first diameter, and wherein the nozzle comprises a second cylindrical portion comprising a smaller second diameter; and a plunger configured to force bone graft material from the reservoir through the nozzle. The plunger comprises: a plunger body positioned at least partially within the syringe and defining a lumen; a handle coupled to a proximal end of the plunger body and positioned outside the reservoir; and a tamp positioned within the lumen of the plunger body and configured to protrude distally of the plunger into the second cylindrical portion comprising the smaller second diameter.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 5a is a cross sectional view of the bone graft loading device shown in FIG. 4 with the plunger and the tamp retracted, according to embodiments of the present disclosure.

FIG. 5b is a cross sectional view of the bone graft loading device shown in FIG. 4 with the plunger and the tamp in distally extended positions, according to embodiments of the present disclosure.

DETAILED DESCRIPTION

Figure 1:
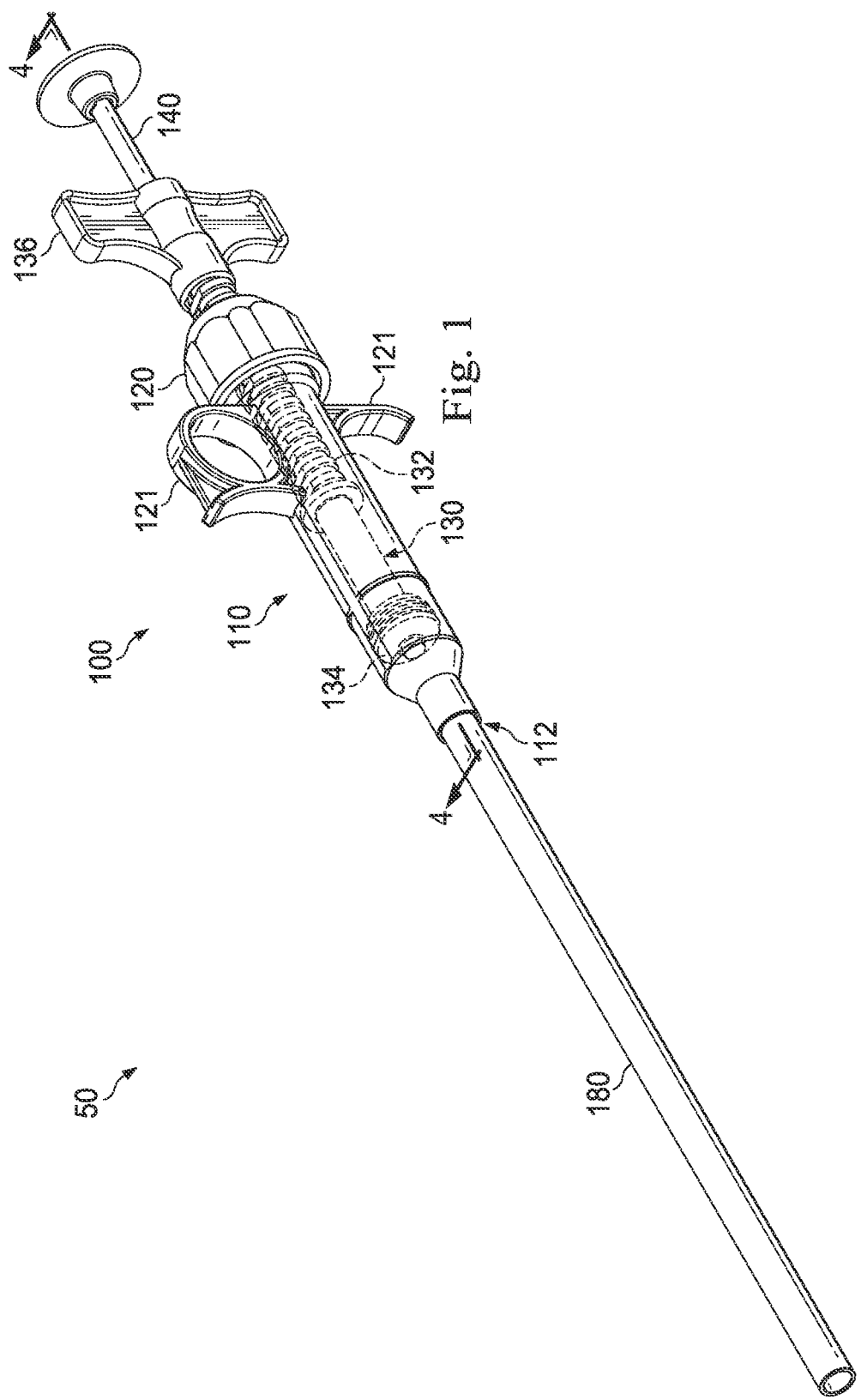
FIG. 1 is a perspective view of a bone graft loading assembly, according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a perspective view of a bone graft delivery assembly 50, according to one embodiment of the present disclosure. The bone graft delivery assembly 50 includes a bone graft loading device 100 and an injection cannula 180. In the illustrated embodiment, the bone graft loading device 100 is configured to load a bone graft material (e.g., allograft) into the cannula 180 for delivery to an operation site of a patient. As described further below, the cannula 180 may be detached from the loading device 100 and coupled to an injection device (e.g., injection device 190, FIG. 2.) for delivery to the operation site.

The loading device 100 includes a syringe body or portion 110, a threaded cap 120 coupled to a proximal end of the syringe body 110, a plunger or plunger body 130 comprising a handle 136 and a threaded portion 132 positioned within the syringe body 110, and a tamp 140 positioned within a lumen of the plunger 130. The loading device 100 shown in FIG. 1 includes two distinct actuation mechanisms for loading bone graft material into the cannula 180: a threaded screw mechanism for advancing the plunger 130 distally within the syringe body 110, and a retractable tamping mechanism for pushing or forcing portions of the bone graft material through a distal opening 112 of the syringe body 110 and into the cannula 180. In that regard, the threaded portion 132 of the plunger 130 engages corresponding threads in a central opening of the threaded cap 120 such that rotating the handle 136 advances the plunger 130 and the tamp 140 distally toward the opening 112 of the syringe body 110. The handle is coupled to a proximal end of the plunger 130 such that the handle 136 is positioned outside the syringe body 110. Additionally, the tamp 140 is configured to be advanced distally within the lumen of the plunger 130 such that a distal end of the tamp 140 protrudes from an opening in a stopper 134 of the plunger 130 toward the opening 112 such that it protrudes at least partially within the cannula 180. These two loading mechanisms can provide both bulk movement and higher force to move the bone graft material into the cannula 180 and a more concentrated tamping mechanism in the event of a clog or stoppage of the bone graft at the distal end of the syringe body 110.

The syringe body 110 includes an integrally formed (e.g., injection molded) hollow body that includes finger grips 121 and the distal opening 112. The syringe body 110 also includes external threads on a proximal end configured to engage with corresponding threads of the threaded cap 120. The syringe body 110 comprises a polymer material and defines a cylindrical or substantially cylindrical reservoir for a bone graft material. It will be understood that any suitable polymer may be used for the syringe body, including polycarbonate, nylon, polyethylene, polypropylene, acrylonitrile butadiene styrene (ABS), polyether ether ketone (PEEK), DELRIN®, or any other suitable material. Further, in some embodiments, the syringe body 110 comprises a metallic material, such as stainless steel, aluminum, brass, or any other suitable metallic material.

The threaded cap 120 is configured to couple to the threads of the syringe body 110. As described further below, the threaded cap 120 includes a second set of central threads configured to engage the threaded portion 132 of the plunger 130. In the illustrated embodiment, the threaded body 120 comprises a polymer material. It will be understood that any suitable polymer may be used for the threaded body 120, including polycarbonate, nylon, polyethylene, polypropylene, ABS, polyether ether ketone (PEEK), DELRIN®, or any other suitable material. Further, in some embodiments, the syringe body 110 comprises a metallic material, such as stainless steel, aluminum, brass, or any other suitable metallic material. In some aspects, it may be advantageous for the threaded cap 120 to include a softer material than the syringe body 110 and/or the threaded portion 132 of the plunger 130 in order to reduce particulates created by friction between the syringe body 110, threaded cap 120, and/or plunger 130. For example, in an exemplary embodiment, the syringe body 110 and the threaded portion 132 of the plunger 130 comprise polycarbonate, and the threaded cap 120 comprises polypropylene.

Figure 2:
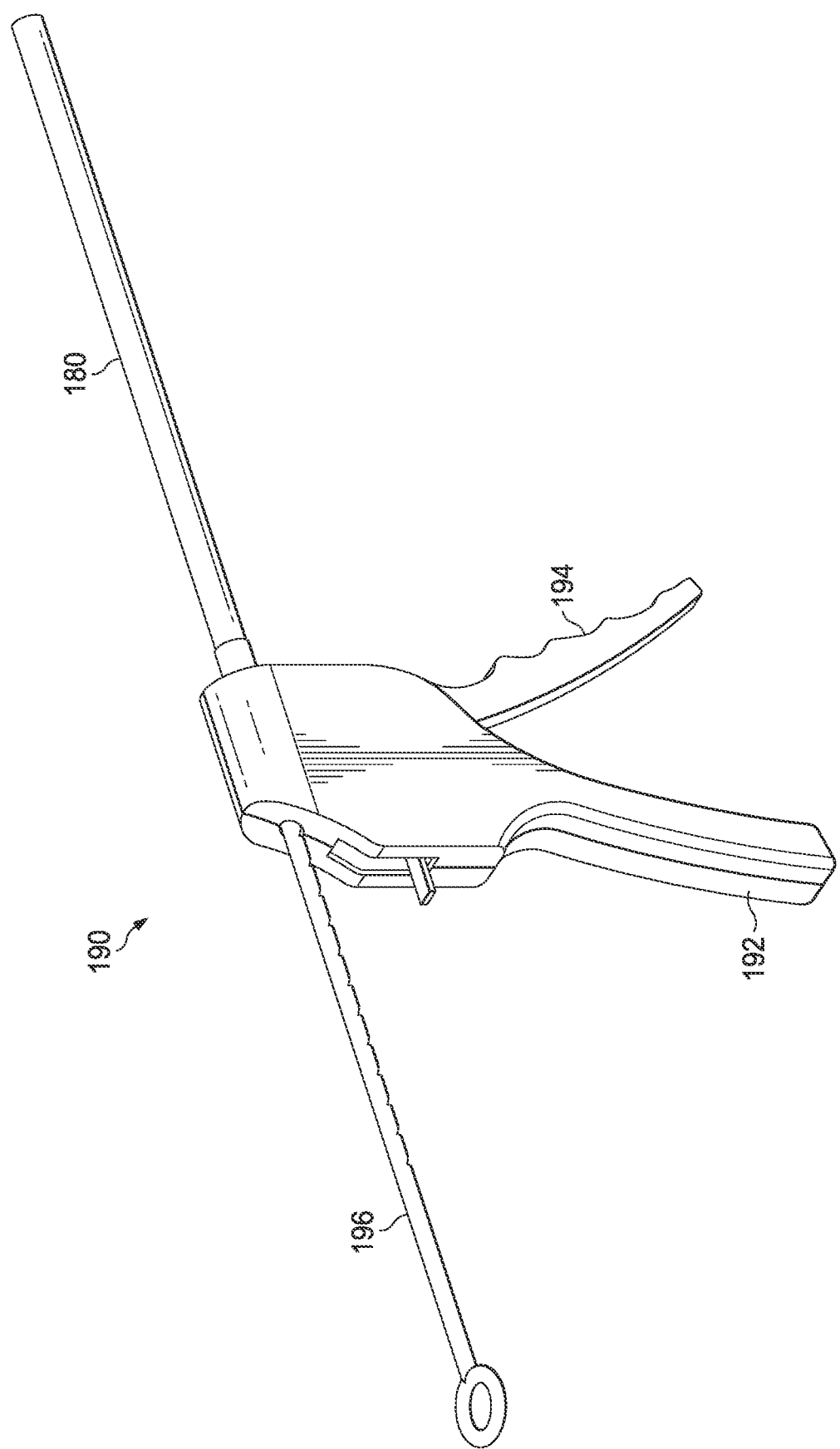
FIG. 2 is a perspective view of a bone graft injection device, according to embodiments of the present disclosure.

FIG. 2 is a perspective view of an injection device 190 coupled to the cannula 180. In that regard, once the cannula 180 has been loaded with bone graft by the loading device 100, the cannula 180 can be attached to the injection device 190 to deliver the bone graft to an operation site of the patient. The injection device 190 comprises a handle 192 and a trigger 194 configured to advance a plunger 196 into the lumen of the cannula 180. In the illustrated embodiment, actuating the trigger 194 causes the plunger 196 to advance forward into the cannula 180. In some embodiments, actuating the trigger 194 causes the plunger to move forward in increments or steps. In that regard, an articulating member may engage threads or grooves on the plunger 196 to move the plunger forward by a controlled amount.

Figure 3:
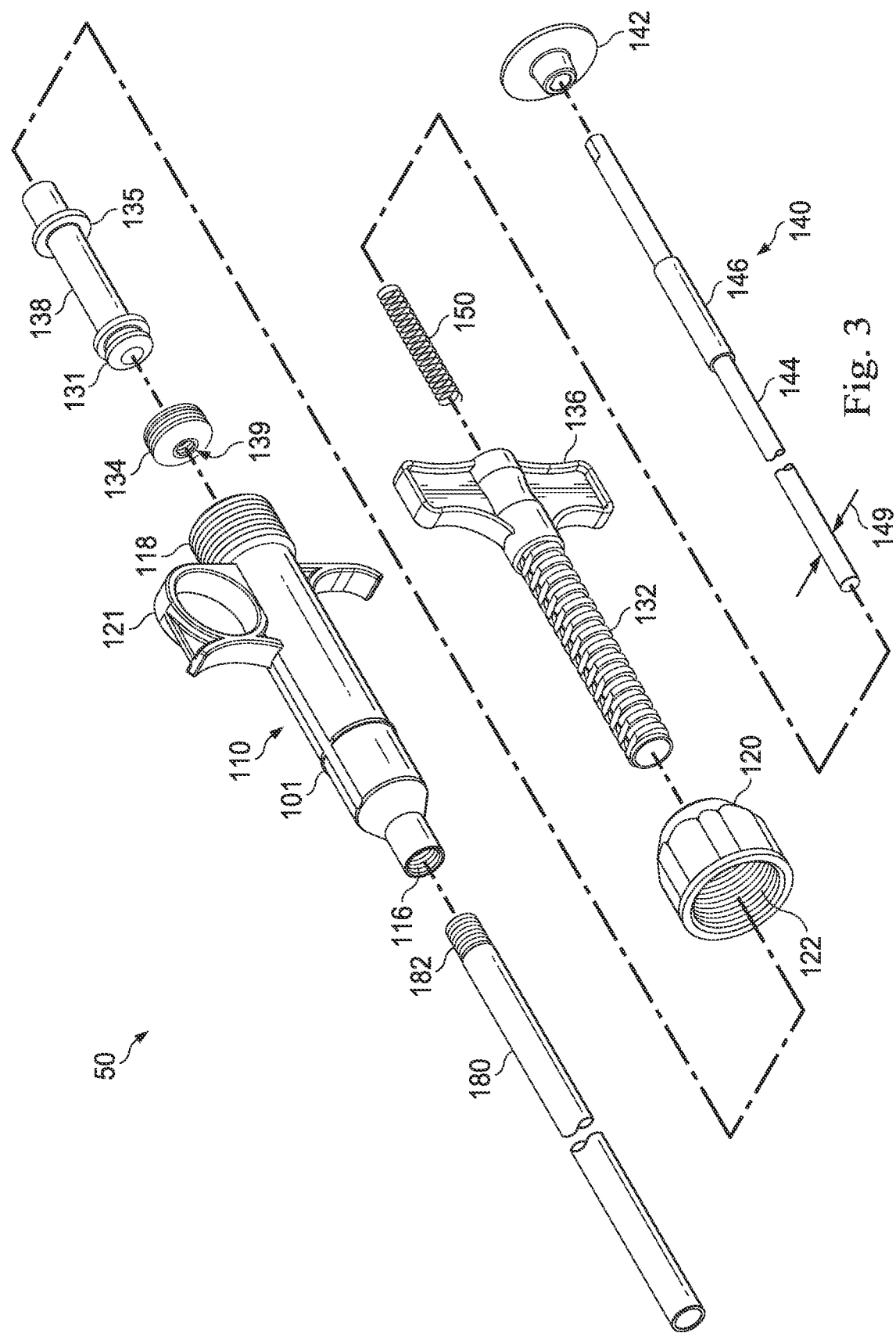
FIG. 3 is an exploded view of a bone graft loading assembly, according to embodiments of the present disclosure.

FIG. 3 illustrates an exploded view of the bone graft injection assembly 50 shown in FIG. 1. Starting at a proximal portion of the assembly 50, a cap 142 is coupled to a proximal end of the tamp body 140, which includes a distal portion 144 and a widened portion 146. In the illustrated embodiment, tamp 140 comprises a single body such that the widened portion comprises an integral part of the tamp 140. However, in other embodiments, the widened portion 146 may comprise a cylindrical body or sheath positioned over the cylindrical tamp body 140. The widened portion 146 is configured to engage a proximal end of a spring such that a distal shelf or end of the widened portion 146 is configured to compress the spring, as further described below. The proximal shelf or end of the widened portion 146 engages a retention feature of the handle 136 such that the tamp 140 is retained within the lumen of the threaded portion 132 of the plunger/handle 136. The tamp 140 and the spring are inserted into the lumen of the threaded portion 132 of the plunger 130. In that regard, it will be understood that the proximal end of the tamp 140 may be inserted into the threaded portion through the distal opening of the threaded portion 132 such that the proximal end of the widened portion abuts the retention feature of the handle 136, as further described below.

The threaded portion 132 is at least partially inserted into the central opening of threaded cap 120 by engaging internal threads of the threaded cap, as further described below. A distal portion 138 or body of the plunger 130 is partially inserted into a distal opening of the threaded portion 132 of the plunger 130. Accordingly, rotating the handle 136 of the plunger 130 relative to the threaded cap 120 advances the threaded portion 132 and the distal portion 138 of the plunger 138 relative to the threaded cap 120. The distal portion 138 includes a retention lip or flange 135 comprising a circular projection and configured to retain the distal portion from being withdrawn from an interior of the syringe body through the threaded cap 120, as further shown below. In that regard, a cross sectional size or diameter of the flange 135 is larger than a cross sectional size or diameter of the central opening (124, FIG. 4) of the threaded cap 120.

In the illustrated embodiment, the handle 136 and the threaded portion 132 of the plunger 130 form single, integral component or body. For example, the threaded portion 132 and the handle 136 may be formed by an injection molding process. In other embodiments, the handle 136 and the threaded portion 132 comprise separate components that may be fused, adhered, welded, screwed, or otherwise coupled to one another. Further, in some embodiments, the distal portion 138 and the threaded portion 132 comprise a single, integrally formed component.

The distal portion 138 of the plunger 130 includes a stopper coupling feature 131 configured to couple to and engage the stopper 134. More specifically, the stopper coupling feature 131 includes at least one projection or lip and at least one groove sized, shaped, and structurally configured to engage a corresponding at least one groove and at least one projection or lip of the stopper 134. The stopper 134 comprises an elastomeric material, such as a silicone rubber, thermoplastic elastomer (TPE), or any other suitable material that can be resiliently deformed to fit over the stopper coupling feature 131. The stopper 134 is sized, shaped, and structurally arranged to form a sliding seal with an inner wall of the syringe body 110. In that regard, an outer surface of the stopper 134 of the plunger 130 is configured to remain in contact with the inner wall of the syringe body 110 around its circumference. Accordingly, the stopper 134 maintains the bone graft material within the portion of the syringe body 110 that is between the stopper 134 and the distal opening 112 while the stopper 134 is advanced distally within the syringe body 110.

The syringe body 110 comprises a first cylindrical portion or section 111 having a larger first diameter. The syringe body 110 further comprises a nozzle 113 that includes a tapered section 114 and a second cylindrical portion or section 115 having a smaller second diameter. The second cylindrical section 115 of the syringe body 110 includes internal threads 116 configured to engage corresponding external threads 182 of the cannula 180. Accordingly, the cannula 180 is attached to the loading device 100 by inserting the threads 182 into the distal opening 112 and rotating the cannula 180 relative to the syringe body 110, or vice versa. The syringe body 110 includes a volume marking 101 to indicate that a particular volume (e.g., 10 mL, 20 mL) of bone graft material is present within the syringe body 110. The volume marking 101 may comprise a projection or raised feature integrally formed (e.g., by injection molding) with the syringe body 110. In other embodiments, the volume marking 101 may comprise visible ink markings printed on the outer surface of the syringe body 110. In some embodiments, no volume markings are used. In other embodiments, multiple volume markings corresponding to different volumes are used.

Assembly of the loading device 100 can be performed as follows. The tamp 140 is inserted through the distal opening of the threaded portion 132 and moved proximally relative to the threaded portion 132 until the widened portion 146 of the tamp 140 abuts the retention feature (e.g., 133, FIG. 4) of the handle 136. The tamp cap 142 is positioned over the proximal end of the tamp 140, aligning the flat surface with a corresponding flat surface of the cap 142. The spring 150 is positioned over the distal portion 144 of the tamp 140 within the lumen of the threaded portion 132. The threaded cap 120 is twisted on to the distal end of the threaded portion 132. The distal portion or body 138 of the plunger 130 is inserted into the distal opening of the threaded portion 132, enclosing the spring within an annular space defined by the distal portion 144 of the tamp 140 and the inner wall of the threaded portion 132. The stopper 134 is coupled to the distal portion 138 of the plunger 130 by positioning the stopper 134 over the retention feature 131. As further shown below, when the distal portion 138 of the plunger 130 is attached to the threaded portion 132, a distal end of the tamp 140 protrudes through an opening 139 of the stopper 134. An inner surface around the opening 139 of the stopper 134 is sized, shaped, and structurally arranged to form a second sliding seal between the stopper 134 and the distal portion of the tamp 140. In this manner, the tamp 140 may be advanced and retracted relative to the stopper 134 while maintaining a seal to prevent bone graft material from escaping into the lumen of the distal portion 138 of the plunger 130. Thus, the stopper 134 provides two sliding seals: a first sliding seal between the stopper 134 and the inner wall of the syringe body 110, and a second sliding seal between the stopper and the outer surface of the distal portion 144 of the tamp 140.

At this stage, the bone graft material may be introduced into the syringe body 110 through the proximal end of the syringe body 110, as further described below with respect to FIG. 7. In some instances, the cannula 180 may be coupled to the syringe body 110 at this stage, or at another stage, either before or after. The partially assembled portion of the loading device that comprises the tamp 140, plunger 130, and threaded cap 120 is coupled to the syringe body 110 by positioning the distal portion 138 and stopper 134 of the plunger 130 within the syringe body 110 and engaging the inner threads 122 of the threaded cap 120 with corresponding external threads 118 of the syringe body 110.

As described further below, the distal portion or section 144 of the tamp 140 comprises a first diameter 149. The first diameter 149 may be sized such that it can protrude through the smaller diameter of the second cylindrical section 115 and into the lumen of the cannula 180. In some embodiments, the diameter 149 of the tamp 140 is approximately equal to the lumen diameter of the cannula 180. In other embodiments, the diameter 149 of the tamp 140 is smaller or larger than the diameter 149 of the tamp 140.

Figure 4:
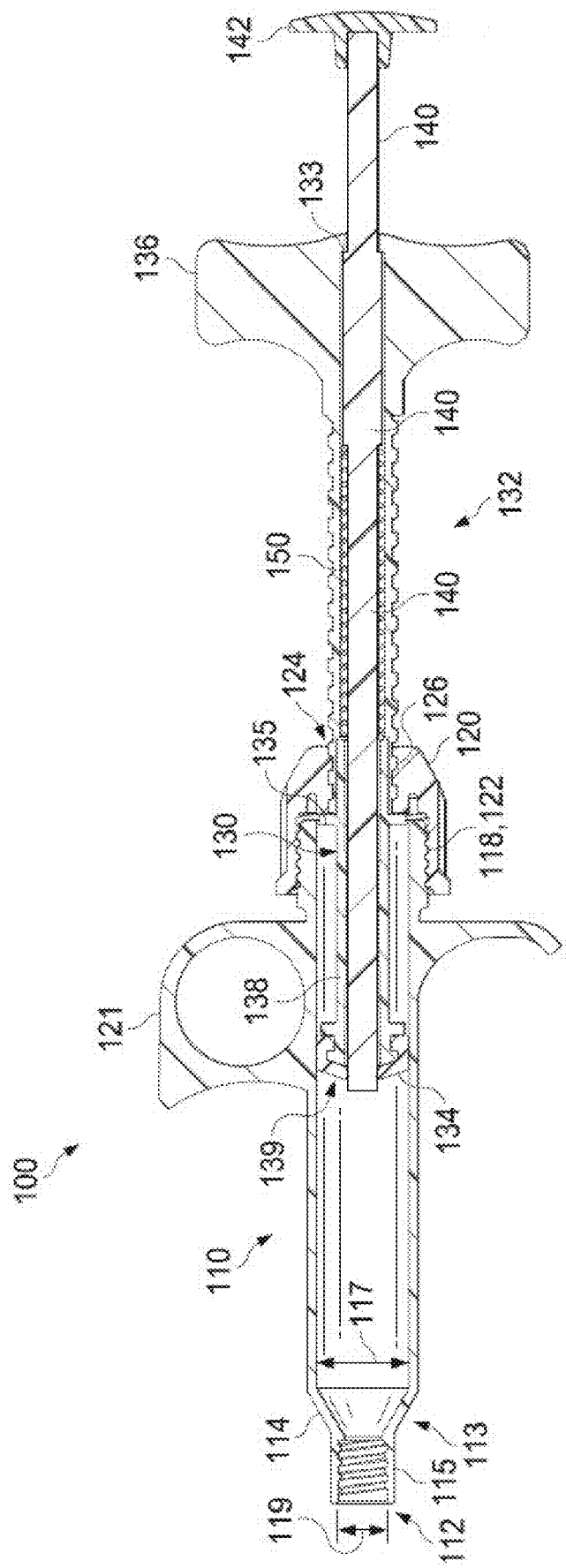
FIG. 4 is a longitudinal cross-sectional view of the bone graft loading device shown in FIG. 1, taken along line 4-4, according to embodiments of the present disclosure.

FIG. 4 shows a longitudinal cross-sectional view of the loading device 100 shown in FIGS. 1 and 3, according to an embodiment of the present disclosure. In particular, FIG. 4 shows additional details related to the two loading mechanisms described earlier. In the illustrated embodiment, the syringe body 110 defines an inner reservoir having a first cylindrical section 111. The first cylindrical section 111 has a first inner diameter 117. The first inner diameter 117 may range from approximately 0.5 in. to approximately 2.0 in., including values such as 0.75 in., 1.0 in., 1.25 in., 1.5 in., or any other suitable value, but larger and smaller. The length of the syringe body 110 may range from approximately 2.0 in. to approximately 8.0 in., including values such as 3.0 in., 4.0 in., 5.0 in., 6.0 in., 7.0 in., or any other suitable value, both larger and smaller. The threaded cap 120 is coupled to the syringe body 110 such that the inner threads 122 of the threaded cap 120 engage corresponding external threads 118 of the syringe body 110. The threaded portion 132 of the plunger 130 is positioned within a central opening 124 of the threaded cap 120 and engages corresponding internal threads 126 within the central opening 124 of the threaded cap 120. The retention lip 135 of the plunger 130 abuts an internal surface of the threaded cap 120 such that the distal portion 138 of the plunger 130 is retained distal of the threaded cap 120. By rotating the handle 136 relative to the threaded cap 120 and syringe body 110, the plunger 130 advances distally further into the syringe body 110. In some aspects, the rotational loading mechanism effected by the threaded plunger 130 and the cap 120 may be used for bulk movement or compacting of the bone graft material to the nozzle 113 and through the distal opening 112 of the syringe body 110. However, as described above, because the second inner diameter 119 is smaller than the first inner diameter 117, the bone graft material may be susceptible to clogs and blockages at or near the nozzle 113. Accordingly, the tamp 140 can be used as described below to break up the clogs and force portions of the bone graft material into the cannula 180.

Referring now to the tamping mechanism, the tamp 140 extends through a lumen of the plunger 130 and a distal end of the tamp 140 extends through a central opening 139 of the stopper 134. In some embodiments, the distal end of the tamp 140 is tapered or rounded. The tamp 140 is sized and shaped to be inserted into the second cylindrical section 115 of the syringe body 110, which has the smaller second diameter 119, through the distal opening 112 of the syringe body 110, and into the cannula 180 (see FIG. 5b). In some embodiment, the tamp 140 is sized and shaped to match a size and shape of the lumen of the cannula 180. For example, in some embodiments, the outer diameter of the tamp 140 is approximately equal to an inner diameter of the cannula 180, which may be equal to, smaller than, or larger than the second diameter 119. In some embodiments, the cross-sectional size of the tamp 140 is slightly smaller than the cross-sectional size of the cannula 180. In some embodiments, the diameter of the tamp 140 ranges from approximately 0.1 in. to about 0.5 in., including values such as 0.125 in., 0.2 in., 0.25 in., 0.3 in., or any other suitable value, both greater or smaller.

The spring 150 is positioned within an annular space defined by the threaded portion 132 of the plunger 130 and the tamp 140. The spring 150 extends from the widened portion 146 of the tamp 140 to the proximal end of the distal portion 138 of the plunger 130. In the illustrated embodiment, the spring 150 is partially compressed and the tamp is maintained in place by the retention feature 133 of the handle 136. Accordingly, the tamp 140 is configured to longitudinally move or translate relative to the syringe body 110 by an amount of travel. In some embodiments, the amount of travel the tamp 140 may travel is at least partially defined by the length of the annular space in which the spring 150 is positioned when the widened portion 146 of the tamp 140 is resting against the retention feature 133 of the plunger 130. In that regard, the tamp 140 may extend distally by compressing the spring 150 until the pitch of the coil spring 150 is closed such that the spring 150 is fully compressed. In the illustrated embodiment, the total travel of the tamp 140 is approximately 1 inch. However, the travel of the tamp 140 may comprise values between approximately 1.0 in. and approximately 2.0 in, or any other suitable amount, including 0.5 in., 0.75 in., 1.25 in., 1.5 in., 1.75 in., 2.25 in., 2.5 in., 3.0 in., 5 in., 6 in., 9 in., or any other suitable value, both larger and smaller. The travel of the tamp 140 may be configured such that, when the plunger 130 is in the position shown in FIG. 4 relative to the syringe body 110, the tamp 140 can be advanced to protrude through the distal opening 112 and partially within the proximal end of the cannula 180. In other embodiments, the tamp 140 can be configured to extend further within the cannula 180 than what is shown in FIGS. 1-4. For example, in some embodiments, the arrangement of the tamp 140 is such that its travel is sufficient to extend through an entire length, or a majority of the length, of the cannula 180. In that regard, in some embodiments the tamp 140 can be used to inject or deliver the bone graft material to the predetermined location in the patient's body.

In FIG. 4, the plunger 130 is shown in a fully retracted position whereby the retention lip 135 is abutting the inner surface of the threaded cap 120. The plunger 130 is configured to be advanced distally within the syringe body 110 until the stopper 134 abuts the inner surface of the nozzle 113 of the syringe body 110. The shape of the distal surface of the stopper 134 at least partially conforms to the shape of the nozzle 113 of the syringe body 110. The convex shape of the stopper 134 may facilitate improved loading because there is less open space remaining when the plunger 130 is fully advanced within the syringe body 110. In some embodiments, the plunger 130 may have approximately the same amount of travel relative to the syringe body 110 as the tamp 140 has relative to the plunger 130. In some embodiments, the amount of travel afforded to the tamp 140 and/or the plunger 130 may differ from what is shown in FIG. 4. For example, in some embodiments, the tamp 140 has a sufficient amount of travel to extend further within the cannula 180 when the plunger 130 is fully retracted. In some embodiments, the tamp 140 and/or the plunger 130 has less travel than that shown in FIG. 4.

FIGS. 5a and 5b illustrate the loading device 100 having bone graft material added within the syringe body 110 with the plunger 130 and the tamp 140 in different loading positions. In FIG. 5a, both the plunger 130 and the tamp 140 are fully retracted such that the stopper 134 of the plunger 130 and the distal end of the tamp 140 are at a first position 141. In FIG. 5b the plunger 130 is partially advanced to a second position 143 and the tamp 140 is fully extended relative to the plunger 130 to a third position 145 such that the tamp 140 extends partially within the cannula 180. The bone graft material 160 may be at least partially compressible. In that regard, in FIG. 5a, bone graft material 160 may be in an uncompressed state such that there are pockets of empty space within the bone graft material. When the plunger 130 and tamp 140 are in the first position 141, the travel of the tamp 140 is not sufficient to reach the distal opening 112 or the cannula 180. The plunger 130 can be advanced distally to compress the bone graft material and force the bone graft material through the distal opening into the cannula 180. However, as mentioned above, the heterogenous nature of the bone graft material 160 may cause it to be susceptible to clogs at the nozzle 113 of the syringe body 110. If too much compressing force is applied on the bone graft material 160 by the plunger 130, the liquid within the bone graft material 160 may be expressed, which undesirably affects the characteristics and workability of the material 160. Accordingly, the tamp 140 can be used to clear clogs in the distal opening and force a smaller amount of bone graft material into the cannula 180.

FIG. 5b shows the loading device 100 with the plunger 130 partially advanced by rotating the handle relative to the threaded cap and syringe body. The tamp 140 is fully advanced by its full travel distance 147 such that the spring is fully compressed and the distal end of the tamp 140 extends through the opening 112 and into the lumen of the cannula 180. The lumen of the cannula 180 comprises a diameter 184. In some embodiments, the travel distance 147 is between approximately 0.25 in., and 6 in. For example, the travel distance 147 may be 0.5 in., 0.75 in., 1.0 in., 1.12 in., 1.25 in., 1.5 in., 2.0 in., 3.0 in., 4.0 in., or any other suitable distance, both greater and smaller. The diameter of the tamp 140 (see 149, FIG. 4) is sized such that it fits within the diameter 184 of the cannula 180. The spring-loaded action of the tamp 140 allows for a separate force mechanism to move the bone graft material into the cannula 180. Accordingly, each force mechanism can be applied independently using different structural features. In that regard, the threaded plunger 130 can be advanced relative to the syringe body by rotating the handle 136 relative to the syringe body and/or threaded cap. When the handle 136 is rotated, the tamp 140 moves distally with the plunger 130 but does not advance distally relative to the plunger. Additionally, the tamp 140 can be advanced distally by pressing on the cap 142 to control the spring-loaded motion of the tamp relative to the plunger 130 and the syringe body 110. When the tamp 140 is fully extended, as shown in FIG. 5b, the distal end of the tamp 140 protrudes through the distal opening 112 of the syringe body 110 and into the cannula 180. In that regard, the syringe body 110 includes a first cylindrical section having a first diameter.

Figure 6:
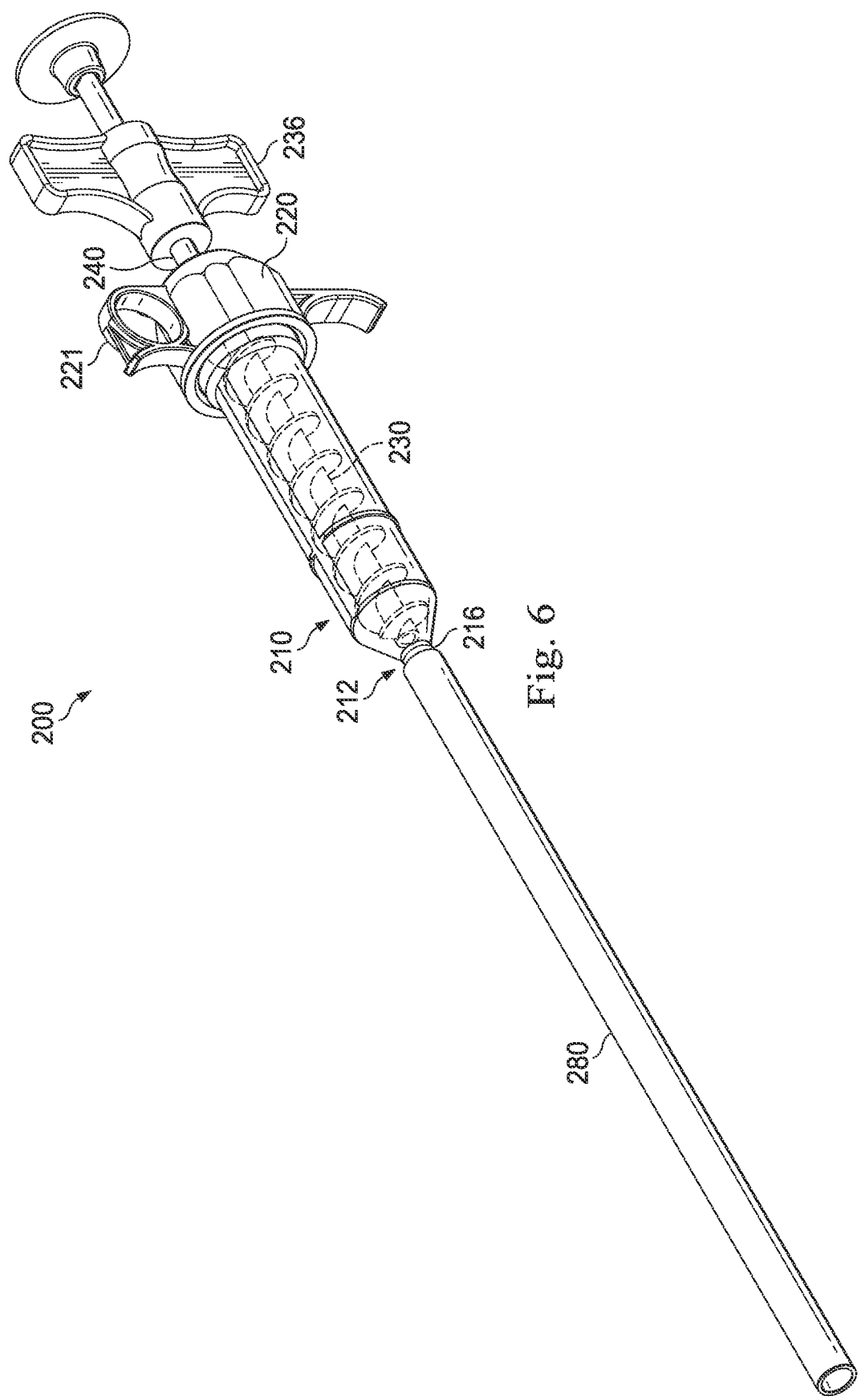
FIG. 6 is a perspective view of a bone graft loading assembly, according to embodiments of the present disclosure.

It will be understood that a number of modifications to the loading device 100 and/or the cannula 180 shown in FIGS. 1-5b can be made without departing from the scope of the original disclosure. FIG. 6 illustrates a loading device 200 and a cannula 280 according to another embodiment of the present disclosure. The loading device 200 may include components similar to the loading device 100 illustrated in FIGS. 1-5b. For example, the loading device 200 comprises a syringe body 210, a threaded cap 220, a tamp 240, a handle 236, and a tamp cap 242. In the embodiment of FIG. 6, an auger-style mechanism 230 is used instead of the threaded plunger described above. In that regard, rotating the handle 236 of the auger 230 causes the auger 230 to rotate, but does not move the auger 230 longitudinally relative to the syringe body 210. In some aspects, the auger style mechanism 230 works with gravity and the inner wall of the syringe body 210 to move bone graft material distally toward the distal opening 212. The tamp 240 is positioned through a central lumen of the auger 230 and can be advanced distally into the cannula 280 to force bone graft material at or near the opening 212 into the cannula 280. Further, in the embodiment of FIG. 6, the finger grips 221 are directly attached to the threaded cap 220 instead of the syringe body 210. At the distal opening 212 of the syringe body 210, the threads 216 are on the outside of the syringe body 210 and on the inside of the cannula 280. In some embodiments, the loading device 200 may include a component within the syringe body 210 that is prevented from rotating within the syringe body 210, but is configured to advance distally within the syringe body 210 as the mechanism 230 rotates to move the bone graft material distally toward the distal opening 212.

It will be understood that various modifications can be made to the loading devices and/or cannulas described above without straying from the scope of the present disclosure. For example, the syringe body may comprise various shapes and/or cross-sectional profiles other than the cylindrical body shown in FIGS. 1-6. In some embodiments, the syringe body comprises a rectangular cross-section, an elliptical cross-section, a triangular cross-section, a polygonal cross-section, or any other suitable shape. The syringe body may comprise various lengths and internal volumes to support various amounts of bone graft material. For example, the syringe body may be sized, shaped, and structurally arranged to contain 5 milliliters (mL) of bone graft material, 10 mL, 20 mL, 30 mL, 50 mL, 100 mL, 200 mL, or any other suitable amount of bone graft material, both greater and smaller. In some embodiments, the syringe includes graduated markings to indicate a volume of material present in the syringe body. In some embodiments, the syringe body 110 can include other openings other than those shown in FIGS. 1-6.

In some embodiments, the plunger body may comprise more or fewer components than shown in the embodiments of FIGS. 1-6. For example, in some embedment's, the plunger 130 comprises a single integral structure. In some embodiments, the threads of the plunger 130 extend along a greater or smaller portion of the length of the plunger, including an entirety of the length of the plunger. In some embodiments, the plunger 130 includes one or more O-rings to create seals between the plunger 130 and the syringe body 110, and/or between the plunger 130 and the tamp 140. In some embodiments, the plunger 130 includes one or more O-rings in lieu of the stopper 134. In an exemplary embodiment, the syringe body 110 and the plunger 130 comprise a same material, such as polycarbonate plastic. However, in other embodiments, the plunger 130 may comprise a different material than the syringe body 110. For example, the plunger 130 may comprise a metallic material, a plastic material, an elastomeric material, a ceramic material, or any other suitable type of material. Similarly, in some embodiments, the plunger 130 may comprise a different material than the threaded cap 120. For example, the threaded cap 120 may comprise a soft plastic material, a metallic material, an elastomeric material, a ceramic material, or any other suitable type of material. In some embodiments, no threaded cap 120 is included in the loading device 100. For example, the syringe body may include internal threads to engage external threads of the threaded plunger 130.

The threaded engagements described herein may vary in some respects. For example, in some embodiments, the threads of the plunger, threaded cap, and/or the cannula comprise right-handed threads. In some embodiments, the threads of the plunger, threaded cap, and/or the cannula comprise left-handed threads. In some embodiments, the threads comprise single lead threads. In some embodiments, the threads comprise double lead threads. While the spring 150 of the loading device 100 is a coil spring, other types of springs may be used for the spring-loaded tamp 140. For example, elastomeric strands may be used to bias the tamp 140 proximally to rest on the retention lip 133. In some embodiments, the stopper 134 may comprise various shapes and/or profiles, including semi-spherical, conical, flat, or any other suitable shape. In some embodiments, the cannula 180 forms an interference fit with the syringe body 110. In some embodiments, the threaded cap forms a locking connection with the syringe body 110.

Figure 7:
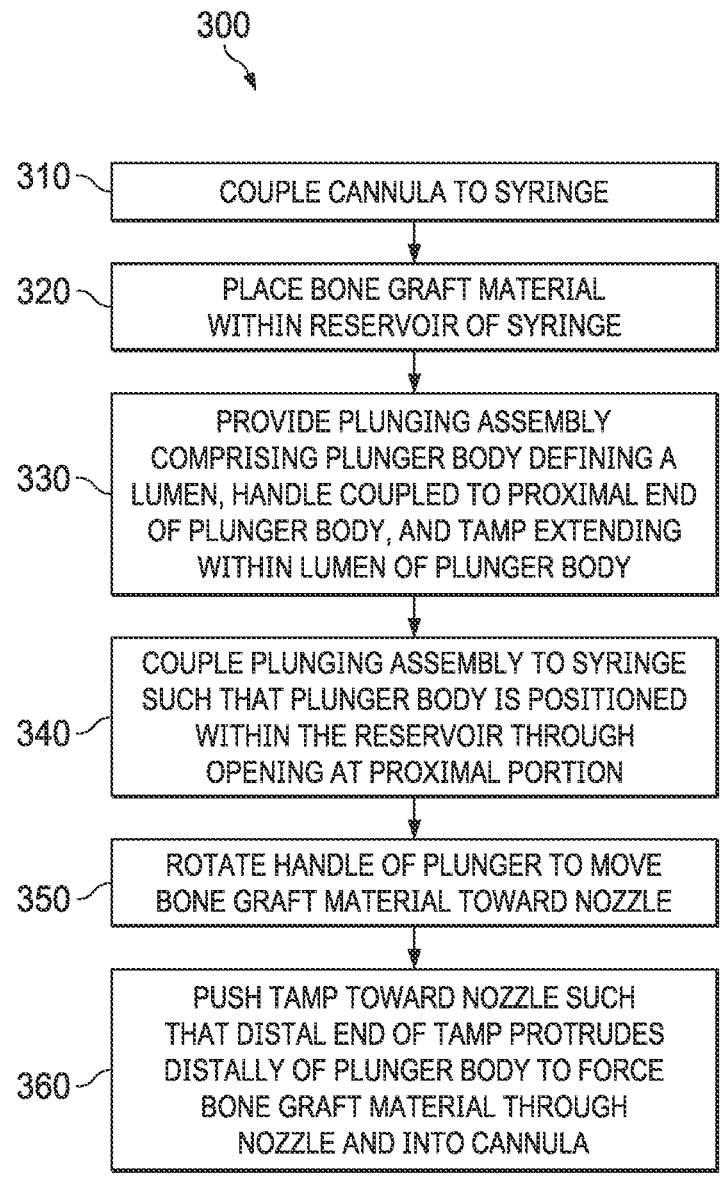
FIG. 7 is a flow diagram illustrating a method for loading bone graft material into a cannula, according to embodiments of the present disclosure.

FIG. 7 is a flow diagram illustrating a method 300 for loading a bone graft material into an injection device using a bone graft loading device. It will be understood that one or more steps of the method may be performed using the devices and/or assemblies described above, including the loading devices 100, 200 and/or the cannulas 180, 280. In step 310, a cannula is coupled to a syringe defining a reservoir, the syringe comprising a nozzle at a distal portion of the syringe and an opening at the proximal portion of the syringe. In step 320, bone graft material is placed within the reservoir. In some embodiments, the bone graft material is added to the reservoir through the opening at the proximal portion of the syringe. In step 330, a plunging assembly is provided that includes a plunger body defining a lumen, a handle coupled to a proximal end of the plunger body, and a tamp extending within the lumen of the plunger body. The tamp is movable relative to the plunger body and biased proximally relative to the plunger body. In step 340, the plunging assembly is coupled to the syringe such that the plunger body is positioned within the reservoir through the opening at the proximal portion. An outer surface of the plunger is configured to form a first sliding seal with the reservoir, and an inner surface of the plunger is configured to form a second sliding seal with the tamp. In step 350, the handle of the plunger assembly is rotated to move the bone graft material toward the nozzle. In step 360, the tamp is pushed distally toward the nozzle such that a distal end of the tamp protrudes distally of the plunger body to force the bone graft material through the nozzle and into the cannula. In some embodiments, the tamp is spring-loaded to create the proximal bias. In some embodiments, the tamp is pushed distally using a tamp cap that is positioned proximal of the handle. Accordingly, the tamp and the plunger body are independently movable to provide two different loading mechanisms, as described above.

Unless explicitly stated otherwise, terms of approximation (e.g., "approximately," "substantially," etc.) can be construed to mean+/−10% of the values stated. Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An apparatus, comprising:
    a cap configured to couple to a syringe, the cap comprising a first threaded portion;
    a plunger coupled to the cap and configured to be positioned within the syringe, the plunger comprising:
        a plunger body, comprising:
            a second threaded portion configured to form a threaded engagement with the first threaded portion of the cap; and
            a lumen extending along a longitudinal axis of the plunger body;
        a stopper coupled to a distal portion of the plunger body; and
        a handle coupled to a proximal end of the plunger body, wherein rotation of the handle causes longitudinal movement of the plunger relative to the cap; and
    a tamp extending through the lumen of the plunger body and configured to move in a longitudinal direction relative to the plunger to protrude distally of the stopper.

2. The apparatus of claim 1, wherein:
    the cap comprises a central opening;
    the first threaded portion is disposed on a periphery of the central opening; and
    the second threaded portion of the plunger body is disposed on an outer surface of the plunger body.

3. The apparatus of claim 1, wherein the distal portion of the plunger body comprises a flange.

4. The apparatus of claim 1, further comprising a spring coupled to the tamp and the plunger, wherein the spring is configured to bias the tamp in a proximal direction relative to the plunger.

5. The apparatus of claim 4, wherein:
the tamp comprises a widened distal section,
wherein the plunger body comprises a first retention feature around the lumen of the plunger body, and
wherein the spring is positioned around the distal section of the tamp and extends between the first retention feature of the plunger body and the widened distal section of the tamp.

6. The apparatus of claim 5, wherein the plunger comprises a second retention feature proximal of the first retention feature, and wherein second retention feature is configured to abut a surface of the widened distal section of the tamp to retain the tamp within the lumen of the plunger body.

7. The apparatus of claim 1, wherein a proximal section of the tamp extends proximally of the lumen of the plunger body, and wherein a tamp cap is coupled to the proximal section of the tamp.

8. The apparatus of claim 7, wherein the tamp cap is positioned proximally of the handle of the plunger and is movable independently of the handle.

9. The apparatus of claim 1, further comprising the syringe.

10. The apparatus of claim 9, wherein the cap further comprises a third threaded portion, wherein the syringe comprises a fourth threaded portion at a proximal portion of the syringe, and wherein the cap is configured to couple to the syringe by a threaded connection between the third threaded portion and the fourth threaded portion.

11. The apparatus of claim 9, wherein the stopper comprises:
a flexible outer surface configured to mate with an inner wall of the syringe; and
a flexible inner surface configured to mate with the tamp.

* * * * *